(12) United States Patent
Saischek

(10) Patent No.: US 8,202,991 B2
(45) Date of Patent: Jun. 19, 2012

(54) PROCESS FOR THE PREPARATION OF 2-FLUOROADENINE

(75) Inventor: Gerald Saischek, Graz (AT)

(73) Assignee: Euticals S.p.A., Lodi (IT)

( * ) Notice: Subject to any disclaimer, the term of this patent is extended or adjusted under 35 U.S.C. 154(b) by 494 days.

(21) Appl. No.: 12/332,723

(22) Filed: Dec. 11, 2008

(65) Prior Publication Data

US 2009/0163713 A1  Jun. 25, 2009

(30) Foreign Application Priority Data

Dec. 12, 2007  (AT) ................................ A 2018/2007

(51) Int. Cl.
*C07D 473/40* (2006.01)
(52) U.S. Cl. ...................................... 544/277
(58) Field of Classification Search .......... None
See application file for complete search history.

(56) References Cited

U.S. PATENT DOCUMENTS 4,188,378 A   2/1980 Montgomery
4,210,745 A   7/1980 Montgomery

FOREIGN PATENT DOCUMENTS

DE   4141454   5/1998

OTHER PUBLICATIONS

Eaton et al, J. Organic Chem 34 747 (1969).*
Abdullah, The Malaysian Journal of Analytical Sciences vol. 12 No. 1 (2008).*
Calley N. Eaton et al. "Convenient Synthesis of 2-Fluoroadenine", The Journal of Organic Chemistry,(1969); 34; pp. 747.
J.A. Montgomery et al. "Synthesis of Potential Anticancer Agents. XX. 2-Fluoropurines", The Journal of American Chemical Society (1960); 82; pp. 463.
Georges A. Olah, "Synthetic methods and reactions. 63. Pyridinium poly(hydrogen Fluoride) (30% pyridine-70% hydrogen fluoride); a convenient reagent for organic fluorination reactions", The Journal of Organic Chemistry (1979); 44; pp. 3872.
Morris J. Robins et al. "Nucleic acid related compounds. 34. Non-aqueous diazotization with tert-butyl nitrite. Introduction of fluorine, chlorine, and bromine at C-2 of purine nucleosides", Canadian Journal of Chemistry (1981); 59; pp. 2608.

* cited by examiner

*Primary Examiner* — Mark Berch
(74) *Attorney, Agent, or Firm* — Steinfl & Bruno LLP

(57) ABSTRACT

A process for the preparation of 2-fluoroadenine with a purity of at least 98% (HPLC Area) is presented. Such very high purity degree of at least 98% (HPLC Area) is obtained directly on the crude product after reacting 2,6-diaminopurine in an amount of anhydrous fluorinating agent; heating the resulting reaction mixture; quenching the heated reaction mixture; separating the solid obtained thereby; and washing and separating the solid, without recrystallization and/or any further purification steps.

14 Claims, No Drawings

PROCESS FOR THE PREPARATION OF 2-FLUOROADENINE

CROSS REFERENCE TO RELATED APPLICATIONS

The present application claims priority to Austrian patent application A 2018/2007 filed on Dec. 12, 2007, the contents of which are incorporated by reference in their entirety.

FIELD

The present disclosure relates to 2-fluoroadenine. More in particular, it relates to a process for the preparation of 2-fluoroadenine with at least 98% purity (HPLC area), wherein this very high purity of at least 98% (HPLC area) is obtained directly on the crude product after washing and filtration, without recrystallization or any further purification steps.

BACKGROUND

2-Fluoroadenine is an intermediate product for the preparation of 2-fluoroadenosine, an important antitumor agent.

It has been known for a long time that fluorine can be introduced through replacement of the amino group in aromatic or heterocyclic compounds via diazonium compounds [Methoden der Organischen Chemie; Houben-Weyl; Volume V/3 (1962); page 213ff].

For the diazotation a suitable nitrite, such as an organic alkyl nitrite, in particular a tertiary alkyl nitrite, like t-butyl nitrite, or an alkali metal nitrite, such as lithium, sodium or potassium nitrite is used. As fluorinating agents, hydrofluoric acid and hydrofluoric acid-amine complexes, such as pyridine-HF (Georges A. Olah; J. Org. Chemie (1979); 44; 3872ff) and tetrafluoroborate in the Schiemann reaction are used.

The reaction—diazotation with simultaneous fluorination—is carried out mainly under as anhydrous conditions as possible [Morris J. Robins, Bogdan Uznanski; Can. J. Chem (1981); 59; 2608].

Preferred methods are usually sodium nitrite in pyridine-hydrofluoric acid complex or in anhydrous hydrofluoric acid.

The selective introduction of fluorine through diazotation of 2,6-diaminopurine in the presence of a fluorinating agent according to Schiemann to give 2-fluoroadenine is already disclosed by J. A. Montgommery et al. in J. Amer. Chem. Soc. (1960); 82; 463 ff. The way for carrying out the reaction and the work-up therein disclosed are completely unacceptable for technical use. The yields are around 6% and the purity around 90%.

A slightly improved method, i.e. the reaction in anhydrous HF, with a slightly higher yield of 22%, is disclosed by Calley N. Eaton et al. in J. Org. Chem. (1969); 34; 747ff. The reaction—diazotation and fluorination—is carried out at 0° C. For the work-up, the residual HF is distilled off and after that the residue is first stirred with water. In order to reach the final purity of "analytically pure", a further filtration on charcoal is carried out.

The selectivity of the introduction of fluorine in position 2 of 2-aminoadenosine is disclosed both on O-protected nucleosides by Morris J. Robins et al. in Can. J. Chem. (1981); 59; 2608ff, and by J. A. Montgomery in U.S. Pat. No. 4,188,378 and U.S. Pat. No. 4,210,745, and by H. Verbrüggen et al. in DE 4141454A1 on unprotected nucleosides.

If selective introduction of fluorine either on 2-aminoadenine or on 2-aminoadenosine, in protected or unprotected sugar portions, are carried out according to one of the available methods so far disclosed, the desired 2-fluoroadenine or 2-fluoroadenosine (O-protected or unprotected) can be obtained in poor yields only after difficult isolation from the reaction solution. Such work-up steps comprise mainly neutralisation of the reaction solution followed by extraction of the crude product from the reaction solution, or distillation of the HF in excess and suitable further purification of the obtained crude product.

According to the known methods, the further purification in order to reach the desired purity degree of at least 98% (HPLC Area), occurs only through further additional steps, such as column chromatography, purification on active charcoal or through recrystallization.

SUMMARY

According to an aspect of the present disclosure, a process for preparation of 2-fluoroadenine is provided, comprising: a) reacting 2,6-diaminopurine in an anhydrous fluorinating agent in presence of nitrite in a temperature range between $-30°$ C. and $-10°$ C.; b) after the addition of the nitrite, heating the reaction mixture for a time interval between 0.5 hours to 4 hours, to a temperature from $-5°$ C. to $+5°$ C.; c) quenching the heated reaction mixture with an added amount of water, expressed in kilograms, 7 to 13 times the amount of fluorinating agent expressed in kilograms; d) separating the solid obtained thereby; e) washing the solid 4 to 7 times with the added amount of water; and f) further separating the solid obtained thereby and, in absence further additional purification steps, drying the solid under vacuum at a temperature of from 70° C. to 85° C., whereby 2-fluoroadenine is obtained in a yield of from 53% to 68%, and with a purity of at least 98% (HPLC area).

Further aspects of the present disclosure are shown in the specification and claims of the present application.

DETAILED DESCRIPTION

It has now surprisingly been found that, in accordance with the teachings of the present disclosure, by use of suitable reaction and work-up conditions, 2-fluoroadenine can be obtained directly from the reaction mixture with higher yields and with a purity degree of at least 98% (HPLC), without additional work-up steps like neutralisation, column chromatography, purification on active charcoal, recrystallization or other purification methods.

This is even more surprising, because the yield of the desired reaction product is not around 100%, but any kind of side products which are present in the reaction mixture are removed during the work-up steps with the selected work-up methods, and clearly 2-fluoroadenine is not simultaneously washed away with them in relevant amounts, therefore it can be obtained directly from the aqueous reaction mixture through easy filtration and adequate washing with demineralised water in notably higher yields, in the range of 50% to 70%, with respect to the methods published so far.

In accordance with the present disclosure, the reaction is carried out without addition of solvents directly in the fluorinating agent, which is used in excess.

The reaction is advantageously carried out in HF/Pyridine. The excess of HF/Pyridin with respect to 2,6-diaminopurine amounts from 2.3- to 6-fold the molar amount in kilograms with respect to the amount of the added 2,6-aminopurine. Preferably, the molar ratio of HF/pyridine means from 3- to 4-fold the moles of 2,6-diaminopurine.

As fluorinating agent HF/Piridine is used. The content of complex HF—HF/Pyridine should amount from 50 to 70 percent by weight. Preferably, the pyridine complex should contain from 65 to 70 percent by weight of HF.

As diazotation reagents organic nitrites, like alkyl nitrites, such as isobutyl nitrite or t-butyl nitrite, preferably t-butylnitrite or alkali metal nitrites like $NaNO_2$, $KNO_2$ or $LiNO_2$, preferably $NaNO_2$, are used.

The addition of 2,6-diaminopurine to the HF/Pyridine solution is carried out at temperatures between −30° C. and +25° C., but preferably at temperatures in the range from 0° C. to +20° C. The addition is carried out in small portions, so that the established temperature limit values, due to the warming of the solution, are possibly not exceeded in the higher temperature limit value. Preferably, the addition is carried out step-by-step using aliquots of the same amounts. The time for the addition of diaminopurine in HF/pyridine is not relevant for the process. It is only important that the higher temperature limit is possibly not exceeded. Short exceedings of the higher temperature limit for a short time do not affect the process.

The addition of the diazotation reagent takes place continuously in the case of liquid substances, or semi-continuously step by step with small and equal amounts of reagent. The respective amounts of addition of solid substances lie between $1/70$ to $1/120$, preferably around $1/100$, with respect to the starting amount of nitrite in kilograms. The addition of aliquots takes place after equal time intervals between 2 and 10 minutes per addition, preferably around 5 minutes, over the entire addition time. In the case of liquid substances, the addition takes place continuously with a dosing rate of $1/300$ to $1/600$, preferably at $1/420$, per minute, with respect to the starting amount (liters or kilograms).

The reaction (diazotation and fluorination) is carried out at temperatures between −30° C. and −10° C., preferably in the range from −20° C. to −12° C.

After completion of the reaction, the reaction mixture is warmed continuously for about 1.5 hours at a temperature of from −5° C. to +2° C., preferably at 0° C.

At the end of the reaction, the reaction mixture warmed at −5° C. to +2° C. is poured quickly into a second reactor and quenched in an amount of water pre-cooled from 2 to 5° C. under vigorous stirring. The amount of pre-cooled water lies between 7- to 13-fold, preferably 8-fold, in kilograms with respect to the added amount of HF/pyridine in kilograms. After about 10-15 minutes stirring the product is filtered, the mother liquor is removed, the 2-fluoroadenine is transferred back again in the reactor, with the same amount of water, processed as above, stirred and filtered again.

This washing procedure is carried out five times in total.

After the final washing the product (2-fluoroadenine) is dried under vacuum at about 70° C. to 80° C. until constant weight.

The yield amounts to 55 to 65%. The purity degree of the purified product is at least 98% (HPLC area) and does not require any further purification step.

In order for the process in accordance with the disclosure to operate, on the one hand the strict compliance with the above-mentioned limits of reaction temperature between −30 to −10° C., preferably from −20 to −12° C., and on the other hand the very high dilution grade by pouring the reaction solution in the appropriate amount of water, are important. This makes it possible to keep the protonation degree of 2-fluoroadenine as low as possible-2-fluoroadenine losses are reduced- and to simultaneously wash away any kind of side products in a satisfactory way. Furthermore, the distillation of the excess of fluorinating agent is avoided, which certainly accounted for the remarkable yield losses in the known processes.

Therefore, the present disclosure provides a process for the synthesis of highly pure 2-fluoroadenosine with at least 98% purity (HPLC-Area) and in high yields in the range of 53% to 68%, without any further purification, like for example preparative HPLC, filtration on active charcoal or recrystallization.

The following examples illustrate, without limitation, the teachings of the present disclosure in greater detail.

EXAMPLE 1

2.45 kg (16.158 mol) 2,6-diaminopurine are added to 12.78 kg (48.474 mol) HF/pyridine (70% by weight) at about 15° C. in small, equal portions under vigorous stirring, over about 50 minutes. Thereafter, the reactor content is cooled to −15° C. 2.17 Kg (18.905 Mol) t-Butyl nitrite are poured in this suspension over about 7 hours, in continuous with a dosing rate of about 5.16 g/min through a pump. At the end of the reaction the reactor temperature is brought to 0° C. in about 90 minutes. 110 Litres demineralised $H_2O$ are placed in a second reactor, cooled to about 2° C. and the reaction mixture from the first reactor is quickly poured in the water. The dilution or hydration warming is negligible. After about 10 minutes the precipitated 2-fluoroadenine is filtered and the mother liquor is discarded. The solid is transferred back in the reactor, stirred again in 110 liters demineralised water $H_2O$ and filtered.

The washing procedure is carried out five times in total.

The properly washed product is dried in a vacuum oven at about 75° C. until constant weight. 1.46 kg 2-fluoroadenine is obtained. Purity: 99.2% (HPLC area). The yield amounts to 59%.

EXAMPLE 2

2.54 kg (16.73 mol) 2,6-diaminopurine is added to 13.24 kg (50.205 Mol) HF/Pyridine (70% by weight) at about 15° C. in small, equal portions under vigorous stirring, over about 50 minutes. Thereafter, the reactor content is cooled to −15° C. In this suspension, 1.390 kg (19.58 Mol) $NaNO_2$ is added over about 7 hours, in 0.0165 kg aliquots every 5 minutes. At the end of the reaction the reactor temperature is warmed up to 0° C. in about 90 minutes. 120 Litres demineralised $H_2O$ is placed in a second reactor, cooled to about 2° C. and the reaction mixture from the first reactor is quickly poured in the water. The dilution or hydration warming is negligible. After about 10 minutes the precipitated 2-fluoroadenine is filtered and the mother liquor is discarded. The solid is transferred back in the reactor, further poured in 120 Litres demineralised $H_2O$ and filtered.

The washing procedure is carried out five times in total.

The properly washed product is dried in a vacuum oven at about 80° C. until constant weight. 1.43 kg 2-Fluoroadenine is obtained. Purity: 99.0% (HPLC-Area). The yield amounts to 56%.

The examples set forth above are provided to give those of ordinary skill in the art a complete disclosure and description of how to make and use the embodiments of the process of the disclosure, and are not intended to limit the scope of what the inventors regard as their disclosure. Modifications of the above-described modes for carrying out the disclosure that are obvious to persons of skill in the art are intended to be within the scope of the following claims.

All patents and publications mentioned in the specification are indicative of the levels of skill of those skilled in the art to which the disclosure pertains.

All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the present application is hereby incorporated herein by reference.

It is to be understood that the disclosures are not limited to particular processes, compositions or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. A process for preparation of 2-fluoroadenine, the method comprising:
   a) reacting 2,6-diaminopurine in an amount of anhydrous fluorinating agent, the reacting performed in presence of nitrite at a temperature range between −30° C. and −10° C. to produce a reaction mixture;
   b) heating the reaction mixture for a time interval between 0.5 hours to 4 hours, to provide a heated reaction mixture at a temperature from −5° C. to +5° C.;
   c) quenching the heated reaction mixture with a first added amount of water to obtain a solid, expressed in kilograms, the added amount of water being 7 to 13 times the amount of anhydrous fluorinating agent expressed in kilograms;
   d) separating the solid from the heated reaction mixture;
   e) washing the solid 4 to 7 times with a second added amount of water to obtain a washed solid;
   f) further separating the washed solid in absence of further additional purification steps, and drying the separated washed solid under vacuum at a temperature of from 70° C. to 85° C., to obtain 2-fluoroadenine in a yield of from 53% to 68% with respect to the 2,6-diaminopurine, and with a purity of at least 98% (HPLC area).

2. The process according to claim 1, wherein the fluorinating agent is hydrofluoric acid or a complex hydrofluoric acid-pyridine with a fluorine content of 60 to 70% by weight.

3. The process according to claim 1, wherein the nitrite is selected from the group consisting of $LiNO_2$, $KNO_2$, $NaNO_2$ and t-butyl nitrite.

4. The process according to claim 1, wherein the first and/or second added amount of water is demineralized or distilled water.

5. The process according to claim 1, wherein a) occurs between −20° C. and −12° C.

6. The process according to claim 1, wherein the time interval in b) is between 1 and 1.5 hours.

7. The process according to claim 1, wherein the temperature in b) is 0° C.

8. The process according to claim 1, wherein the first added amount of water is 8 times the amount of fluorinating agent.

9. The process according to claim 1, wherein at least one between d) and f) includes filtering.

10. The process according to claim 1, wherein e) is performed 5 times.

11. The process according to claim 1, wherein drying under vacuum in f) occurs at a temperature of 80° C.

12. The process according to claim 1, whereby 2-fluoroadenine is obtained in a yield of from 54% to 60% with respect to the 2,6-diaminopurine.

13. The process according to claim 2, wherein the fluorine content is 70% by weight.

14. The process according to claim 3, wherein the nitrite is selected from the group consisting of t-butyl nitrite and $NaNO_2$.

* * * * *